(12) United States Patent
Yogeswaren

(10) Patent No.: US 7,513,147 B2
(45) Date of Patent: Apr. 7, 2009

(54) PIEZOCOMPOSITE TRANSDUCER FOR A DOWNHOLE MEASUREMENT TOOL

(75) Inventor: Elan Yogeswaren, Houston, TX (US)

(73) Assignee: PathFinder Energy Services, Inc., Houston, TX (US)

( * ) Notice: Subject to any disclaimer, the term of this patent is extended or adjusted under 35 U.S.C. 154(b) by 529 days.

(21) Appl. No.: 11/390,585

(22) Filed: Mar. 28, 2006

(65) Prior Publication Data

US 2006/0185430 A1 Aug. 24, 2006

Related U.S. Application Data

(63) Continuation-in-part of application No. 10/613,610, filed on Jul. 3, 2003, now Pat. No. 7,036,363.

(51) Int. Cl.
*E21B 47/00* (2006.01)
*E21B 49/00* (2006.01)

(52) U.S. Cl. .................. 73/152.58; 73/152.16; 310/334

(58) Field of Classification Search ............. 73/152.58, 73/152.16; 310/334
See application file for complete search history.

(56) References Cited

U.S. PATENT DOCUMENTS

| | | |
|---|---|---|
| 3,381,267 A | 4/1968 | Cubberly, Jr. et al. |
| 3,493,921 A | 2/1970 | Johns |
| 3,553,640 A | 1/1971 | Zemanek |
| 3,663,842 A | 5/1972 | Miller |
| 3,770,006 A | 11/1973 | Sexton et al. |
| 3,792,429 A | 2/1974 | Patton et al. |
| 3,867,714 A | 2/1975 | Patton |
| 4,382,201 A | 5/1983 | Trzaskos |
| 4,450,540 A | 5/1984 | Mallett |
| 4,485,321 A | 11/1984 | Klicker et al. |
| 4,523,122 A | 6/1985 | Tone et al. |
| 4,543,648 A | 9/1985 | Hsu |
| 4,556,814 A | 12/1985 | Ito et al. |
| 4,571,693 A | 2/1986 | Birchak et al. |
| 4,594,691 A | 6/1986 | Kimball et al. |
| 4,628,223 A | 12/1986 | Takeuchi et al. |
| 4,649,526 A | 3/1987 | Winbow et al. |

(Continued)

FOREIGN PATENT DOCUMENTS

CA 2346546 11/2001

(Continued)

OTHER PUBLICATIONS

McKeighen, R.E., "Design Guidelines for Medical Ultrasonic Arrays", SPIE International Symposium on Medical Imaging, Feb. 25, 1998.

(Continued)

*Primary Examiner*—Hezron E. Williams
*Assistant Examiner*—Rodney T Frank

(57) ABSTRACT

An acoustic sensor for use in a downhole measurement tool includes a piezo-composite transducer element. In various exemplary embodiments, the acoustic sensor further includes a composite backing layer, at least one matching layer, and a barrier layer deployed at an outermost surface of the sensor. Exemplary embodiments of this invention may advantageously withstand the extreme temperatures, pressures, and mechanical shocks frequent in downhole environments and thus may exhibit improved reliability. Exemplary embodiment of this invention may further provide improved signal to noise characteristics. Methods for fabricating acoustic sensors and downhole measurement tools are also provided.

20 Claims, 7 Drawing Sheets

U.S. PATENT DOCUMENTS

| | | | |
|---|---|---|---|
| 4,665,511 A | 5/1987 | Rodney et al. | |
| 4,682,308 A | 7/1987 | Chung | |
| 4,686,409 A | 8/1987 | Kaarmann et al. | |
| 4,698,792 A | 10/1987 | Kurkjian et al. | |
| 4,698,793 A | 10/1987 | Wu | |
| 4,700,803 A | 10/1987 | Mallett et al. | |
| 4,705,981 A | 11/1987 | Inoue et al. | |
| 4,774,693 A | 9/1988 | Winbow et al. | |
| 4,800,316 A | 1/1989 | Ju-Zhen | |
| 4,832,148 A | 5/1989 | Becker et al. | |
| 4,855,963 A | 8/1989 | Winbow et al. | |
| 4,872,526 A | 10/1989 | Wignall et al. | |
| 4,890,268 A | 12/1989 | Smith et al. | |
| 5,027,331 A | 6/1991 | Winbow et al. | |
| 5,036,945 A | 8/1991 | Hoyle et al. | |
| 5,038,067 A | 8/1991 | Tabin | |
| 5,038,069 A | 8/1991 | Lukasiewicz et al. | |
| 5,077,697 A | 12/1991 | Chang | |
| 5,109,698 A | 5/1992 | Owen | |
| 5,130,950 A | 7/1992 | Orban et al. | |
| 5,191,796 A | 3/1993 | Kishi et al. | |
| 5,229,553 A | 7/1993 | Lester et al. | |
| 5,265,067 A | 11/1993 | Chang | |
| 5,278,805 A | 1/1994 | Kimball | |
| 5,331,604 A | 7/1994 | Chang et al. | |
| 5,387,767 A | 2/1995 | Aron et al. | |
| RE34,975 E | 6/1995 | Orban et al. | |
| 5,469,736 A | 11/1995 | Moake | |
| 5,486,695 A | 1/1996 | Schultz et al. | |
| 5,510,582 A | 4/1996 | Birchak et al. | |
| 5,544,127 A | 8/1996 | Winkler | |
| 5,644,186 A | 7/1997 | Birchak et al. | |
| 5,661,696 A | 8/1997 | Kimball et al. | |
| 5,678,643 A | 10/1997 | Robbins et al. | |
| 5,726,951 A | 3/1998 | Birchak et al. | |
| 5,753,812 A | 5/1998 | Aron et al. | |
| 5,784,333 A | 7/1998 | Tang et al. | |
| 5,808,963 A | 9/1998 | Esmersoy | |
| 5,831,934 A | 11/1998 | Gill et al. | |
| 5,844,349 A | 12/1998 | Oakley et al. | |
| 5,852,587 A | 12/1998 | Kostek et al. | |
| 5,899,958 A | 5/1999 | Dowell et al. | |
| 5,936,913 A | 8/1999 | Gill et al. | |
| 5,960,371 A | 9/1999 | Saito et al. | |
| 6,014,898 A | 1/2000 | Finsterwald et al. | |
| 6,067,275 A | 5/2000 | Sayers | |
| 6,082,484 A | 7/2000 | Molz et al. | |
| 6,088,294 A | 7/2000 | Leggett, III et al. | |
| 6,102,152 A | 8/2000 | Masino et al. | |
| 6,107,722 A | 8/2000 | Thurn | |
| 6,147,932 A | 11/2000 | Drumheller | |
| 6,188,647 B1 | 2/2001 | Drumheller | |
| 6,208,585 B1 | 3/2001 | Stroud | |
| 6,213,250 B1 | 4/2001 | Wisniewski et al. | |
| 6,236,144 B1 | 5/2001 | Millar et al. | |
| 6,258,034 B1 | 7/2001 | Hanafy | |
| 6,272,916 B1 | 8/2001 | Taniguchi et al. | |
| 6,308,137 B1 | 10/2001 | Underhill et al. | |
| 6,320,820 B1 | 11/2001 | Gardner et al. | |
| 6,354,146 B1 | 3/2002 | Birchak et al. | |
| 6,396,199 B1 | 5/2002 | Douglas et al. | |
| 6,405,136 B1 | 6/2002 | Li et al. | |
| 6,459,993 B1 | 10/2002 | Valero et al. | |
| 6,467,140 B2 | 10/2002 | Gururaja | |
| 6,477,112 B1 | 11/2002 | Tang et al. | |
| 6,480,118 B1 | 11/2002 | Rao | |
| 6,535,458 B2 | 3/2003 | Meehan | |
| 6,543,281 B2 | 4/2003 | Pelletier et al. | |
| 6,568,486 B1 | 5/2003 | George | |
| 6,607,491 B2 | 8/2003 | Sato | |
| 6,614,716 B2 | 9/2003 | Plona et al. | |
| 6,615,949 B1 | 9/2003 | Egerev et al. | |
| 6,618,322 B1 | 9/2003 | Georgi | |
| 6,625,541 B1 | 9/2003 | Shenoy et al. | |
| 6,654,688 B1 | 11/2003 | Brie et al. | |
| 6,671,380 B2 | 12/2003 | Chang et al. | |
| 6,776,762 B2 | 8/2004 | Erikson et al. | |
| 6,788,620 B2 | 9/2004 | Shiraishi et al. | |
| 6,894,425 B1 | 5/2005 | Solomon et al. | |
| 6,897,601 B2 | 5/2005 | Birth et al. | |
| 6,995,500 B2 * | 2/2006 | Yogeswaren | 310/334 |
| 7,036,363 B2 * | 5/2006 | Yogeswaren | 73/152.16 |
| 7,075,215 B2 * | 7/2006 | Yogeswaren | 310/334 |
| 2002/0062992 A1 | 5/2002 | Fredericks et al. | |
| 2002/0096363 A1 | 7/2002 | Evans et al. | |
| 2002/0113717 A1 | 8/2002 | Tang et al. | |
| 2003/0002388 A1 | 1/2003 | Mandal | |
| 2003/0018433 A1 | 1/2003 | Blanch et al. | |
| 2003/0058739 A1 | 3/2003 | Hsu et al. | |
| 2003/0106739 A1 | 6/2003 | Arian et al. | |
| 2003/0114987 A1 | 6/2003 | Edwards et al. | |
| 2003/0123326 A1 | 7/2003 | Wisniewski et al. | |
| 2003/0137302 A1 | 7/2003 | Clark et al. | |
| 2003/0137429 A1 | 7/2003 | Clark et al. | |
| 2003/0139884 A1 | 7/2003 | Blanch et al. | |
| 2003/0141872 A1 | 7/2003 | Clark et al. | |
| 2003/0150262 A1 | 8/2003 | Han et al. | |
| 2003/0167126 A1 | 9/2003 | Horne et al. | |
| 2005/0006620 A1 | 1/2005 | Helke | |

FOREIGN PATENT DOCUMENTS

| | | |
|---|---|---|
| EP | 0375549 A2 | 6/1990 |
| EP | 1158138 A2 | 11/2001 |
| GB | 2156984 A | 10/1985 |
| GB | 2381847 A | 5/2003 |
| WO | WO0072000 A1 | 11/2000 |

OTHER PUBLICATIONS

Ohm, R.F., "The Vanderbilt Rubber Handbook, 13th Ed.", R.T. Vanderbilt Company, Inc., Nowalk, CT, 1990, pp. 211-222.

Smith, W.A., "New Opportunities in Ultrasonic Transducers Emerging from Innovations in Piezoelectric Materials", SPIE vol. 1733, 1992, pp. 3-26.

Product Literature Obtained from Ohara Corporation, 23141 Arroyo Vista, Santa Margarita, CA, Jul. 2003. http://www.oharacorp.com/swf/ap.html.

Product Literature Obtained from Corning Glass Works Corporation, Houghton Park, New York, Jun. 2003.

Product Literature "Dyneon Fluoroelastomer FE5623", obtained from Dyneon, Decator, Alabama, Jun. 2003.

Product Literature "Dyneon Fluoroelastomer FC2178", obtained from Dyneon, Decator, Alabama, Jun. 2003.

Product Literature "Dyneon Fluoroelastomer FC2181", obtained from Dyneon, Decator, Alabama, Jun. 2003.

Technical Information "Viton®B-50", DuPont Dow elastomers, dated Dec. 1998, Wilmington, Delware 19809.

* cited by examiner

PIEZOCOMPOSITE TRANSDUCER FOR A DOWNHOLE MEASUREMENT TOOL

FIELD OF THE INVENTION

The present invention relates generally to downhole measurement tools utilized for measuring properties of a subterranean borehole during drilling operations. More particularly, this invention relates to an acoustic sensor for use in a downhole measurement tool, the acoustic sensor having one or more piezo-composite transducer elements for transmitting and/or receiving ultrasonic energy during measurement of borehole characteristics.

BACKGROUND OF THE INVENTION

The use of acoustic (e.g., ultrasonic) measurement systems in prior art downhole applications, such as logging while drilling (LWD), measurement while drilling (MWD), and wireline logging applications is well known. In known systems an acoustic sensor, typically with a substantially homogenous piezo-ceramic structure on board, operates in a pulse-echo mode in which it is utilized to both send and receive a pressure pulse in the drilling fluid (also referred to herein as drilling mud). In use, an electrical drive voltage (e.g., a square wave pulse) is applied to the transducer, which vibrates the surface thereof and launches a pressure pulse into the drilling fluid. A portion of the ultrasonic energy is typically reflected at the drilling fluid/borehole wall interface back to the transducer, which induces an electrical response therein. Various characteristics of the borehole, such as borehole diameter and measurement eccentricity and drilling fluid properties, may be inferred utilizing such ultrasonic measurements. For example, U.S. Pat. No. 4,665,511 to Rodney et al., discloses a System for Acoustic Caliper Measurements using ultrasonic measurements in a borehole, while U.S. Pat. No. 4,571,693 to Birchak et al., discloses an Acoustic Device for Measuring Fluid Properties that is said to be useful in downhole drilling applications. Numerous other prior art acoustic measurement systems are available in the prior art, including for example, U.S. Pat. RE 34,975 to Orban et al., U.S. Pat. No. 5,469,736 to Moake, U.S. Pat. No. 5,486,695 to Schultz et al., and U.S. Pat. No. 6,213,250 to Wisniewski et al.

While prior art acoustic sensors have been used in various downhole applications (as described in the previously cited U.S. patents), their use, particularly in logging while drilling (LWD) and measurement while drilling (MWD) applications, tends to be limited by various factors. As used in the art, there is not always a clear distinction between the terms LWD and MWD, however, MWD typically refers to measurements taken for the purpose of drilling the well (e.g., navigation) whereas LWD typically refers to measurement taken for the purpose of analysis of the formation and surrounding borehole conditions. Nevertheless, these terms are hereafter used synonymously and interchangeably.

Most prior art acoustic measurement systems encounter serious problems that result directly from the exceptional demands of the drilling environment. Acoustic sensors used downhole must typically withstand temperatures ranging up to about 200 degrees C. and pressures ranging up to about 25,000 psi. In many prior art systems, expansion and contraction caused by changing temperatures is known, for example, to cause delamination of impedance matching layers and/or backing layers from surfaces of the transducer element. Further, the acoustic sensors are subject to various (often severe) mechanical forces, including shocks and vibrations up to 650 G per millisecond. Mechanical abrasion from cuttings in the drilling fluid, and direct hits on the sensor face (e.g., from drill string collisions with the borehole wall) have been known to damage or even fracture a piezo-ceramic element in the transducer. A desirable acoustic sensor must not only survive the above conditions but also function in a substantially stable manner for up to several days (time of a typical drilling operation) while exposed thereto.

Existing acoustic measurement systems also tend to be limited in downhole environments by transducer ringing and a relatively poor signal to noise ratio (as compared to, for example, transducers used in other applications). As such, typical prior art acoustic sensors are typically imprecise at measuring distances outside of a relatively narrow measurement range. At relatively small distances (e.g., less than about one centimetre) acoustic measurements tend to be limited by residual transducer ringing and other near field limitations related to the geometry of the transducer. At relatively larger distances (e.g., greater than about 8 centimetres) acoustic measurements tend to be limited by a reduced signal to noise ratio, for example, related to the transmitted signal amplitude and the receiver sensitivity required to overcome drilling mud attenuation and formation/mud impedance contrast effects.

Therefore, there exists a need for an improved acoustic sensor for downhole applications. While the above described limitations are often associated with the transducer element (i.e., the piezo-ceramic element in prior art downhole devices), and thus represent a need for improved transducers for down hole applications, there also exists a need for improved impedance matching layers and backing layers (also referred to as attenuating layers) for acoustic sensors utilized in downhole applications. Thus a need especially exists for an acoustic sensor having an improved transducer element, impedance matching layers, and backing layer specifically to address the challenging demands of downhole applications.

SUMMARY OF THE INVENTION

The present invention addresses one or more of the above-described drawbacks of prior art acoustic sensors used in downhole applications. Referring briefly to the accompanying figures, aspects of this invention include a downhole tool including at least one acoustic sensor having a piezo-composite transducer. The piezo-composite transducer may be configured, for example, to withstand demanding downhole environmental conditions. Various exemplary embodiments of the acoustic sensor further include a matching layer assembly for substantially matching the acoustic impedance of the piezo-composite transducer with that of the drilling fluid and for providing mechanical protection for the transducer and/or a backing layer for substantially attenuating ultrasonic energy reflected back into the acoustic sensor. Exemplary embodiments of the downhole tool of this invention include three acoustic sensors disposed substantially equidistantly around the periphery of the tool.

Exemplary embodiments of the present invention advantageously provide several technical advantages. Various embodiments of the acoustic sensor of this invention may withstand the extreme temperatures, pressures, and mechanical shocks frequent in downhole environments. Tools embodying this invention may thus display improved reliability as a result of the improved robustness to the downhole environment. Exemplary embodiments of this invention may further advantageously improve the signal to noise ratio of downhole acoustic measurements and thereby improve the sensitivity and utility of such measurements.

In one aspect the present invention includes a downhole measurement tool. The downhole measurement tool includes a substantially cylindrical tool body having a cylindrical axis. The tool further includes at least one acoustic sensor deployed on the tool body, the acoustic sensor including a piezo-composite transducer element with anterior and posterior faces. The piezo-composite transducer is in electrical communication with an electronic control module via conductive electrodes disposed on each of the faces. The piezo-composite transducer element includes regions of piezoelectric material deployed in a matrix of a substantially non piezoelectric material, the regions extending through a thickness of the transducer element in at least one dimension. In exemplary variations of this aspect, the acoustic sensor includes a laminate having a composite backing layer, at least one matching layer, and a barrier layer deployed at an outermost surface of the acoustic sensor.

In another aspect, this invention includes an acoustic sensor having a piezo-composite transducer element. Further aspects of this invention include a method for fabricating a downhole measurement tool and a method for fabricating an acoustic sensor.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
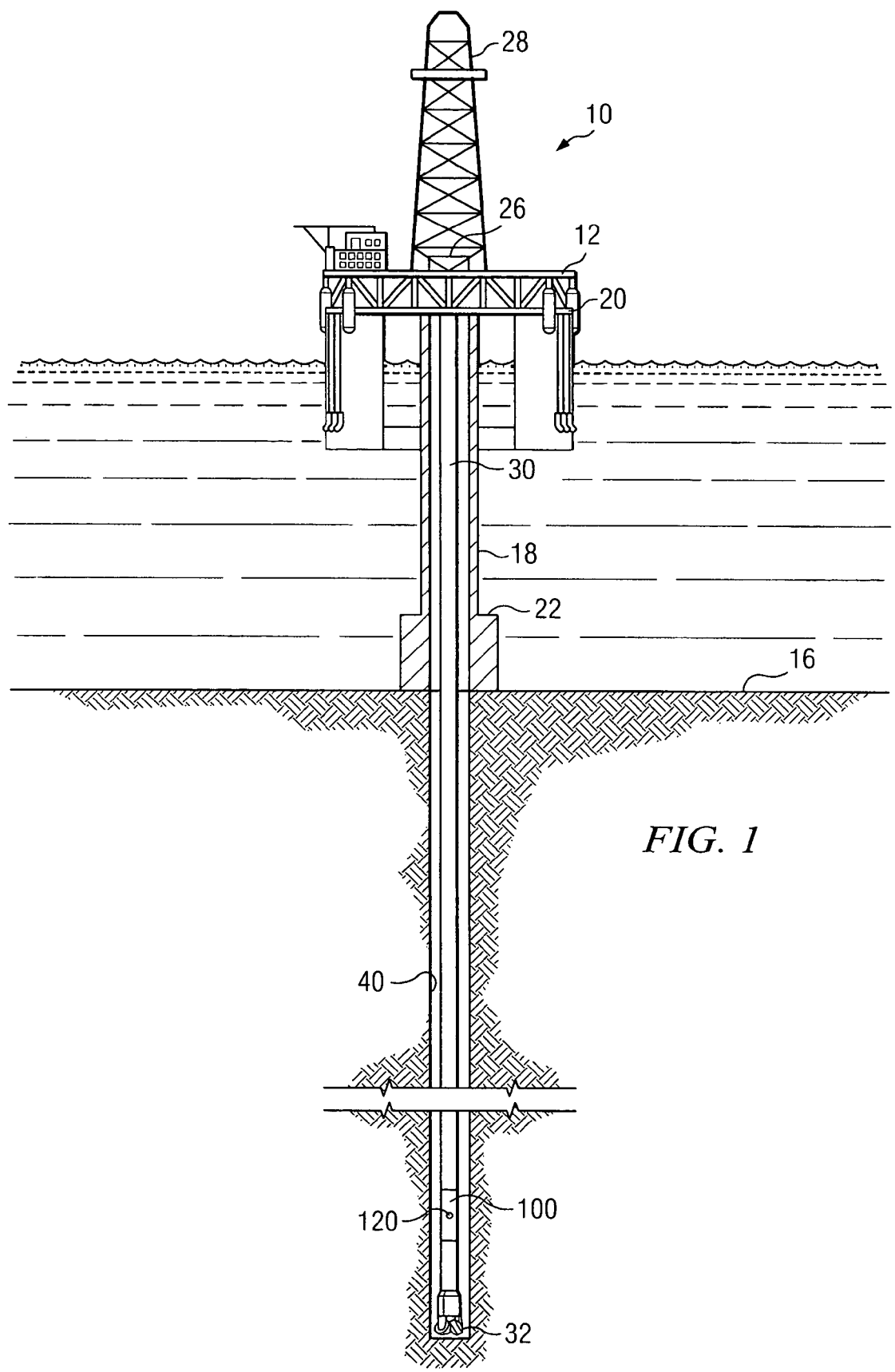
FIG. 1 is a schematic representation of an offshore oil and/or gas drilling platform utilizing an exemplary embodiment of the present invention.

FIG. 1 schematically illustrates one exemplary embodiment of a measurement tool 100 according to this invention in use in an offshore oil or gas drilling assembly, generally denoted 10. In FIG. 1, a semisubmersible drilling platform 12 is positioned over an oil or gas formation (not shown) disposed below the sea floor 16. A subsea conduit 18 extends from deck 20 of platform 12 to a wellhead installation 22. The platform may include a derrick 26 and a hoisting apparatus 28 for raising and lowering the drill string 30, which, as shown, extends into borehole 40 and includes a drill bit 32 and an acoustic measurement tool 100 including at least one acoustic sensor 120. Drill string 30 may further include a downhole drill motor, a mud pulse telemetry system, and one or more other sensors, such as a nuclear logging instrument, for sensing downhole characteristics of the borehole and the surrounding formation.

It will be understood by those of ordinary skill in the art that the measurement tool 100 of the present invention is not limited to use with a semisubmersible platform 12 as illustrated in FIG. 1. Measurement tool 100 is equally well suited for use with any kind of subterranean drilling operation, either offshore or onshore.

Figure 2:
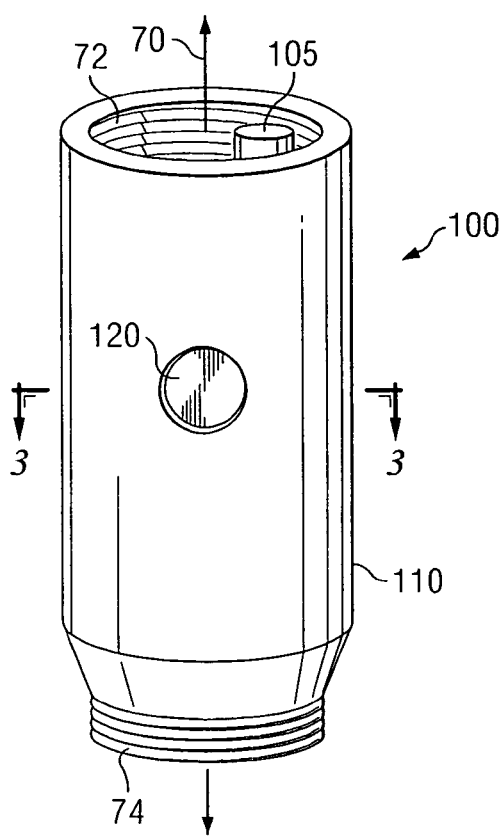
FIG. 2 is a schematic representation of an exemplary MWD tool including an exemplary embodiment of the present invention.

Referring now to FIG. 2, one exemplary embodiment of an acoustic measurement tool 100 according to the present invention is illustrated in perspective view. In FIG. 2, measurement tool 100 is typically a substantially cylindrical tool, being largely symmetrical about cylindrical axis 70 (also referred to herein as a longitudinal axis). Acoustic measurement tool 100 includes a substantially cylindrical tool collar 110 configured for coupling to a drill string (e.g., drill string 30 in FIG. 1) and therefore typically, but not necessarily, includes threaded end portions 72 and 74 for coupling to the drill string. Through pipe 105 provides a conduit for the flow of drilling fluid downhole, for example, to a drill bit assembly (e.g., drill bit 32 in FIG. 1). Measurement tool 100 includes at least one, and preferably three or more, acoustic sensors 120 having a piezo-composite transducer element (not shown in FIG. 2) configured for transmitting and receiving ultrasonic signals. The piezo-composite transducer elements are described in more detail below with respect to FIGS. 4 through 6.

Figure 3:
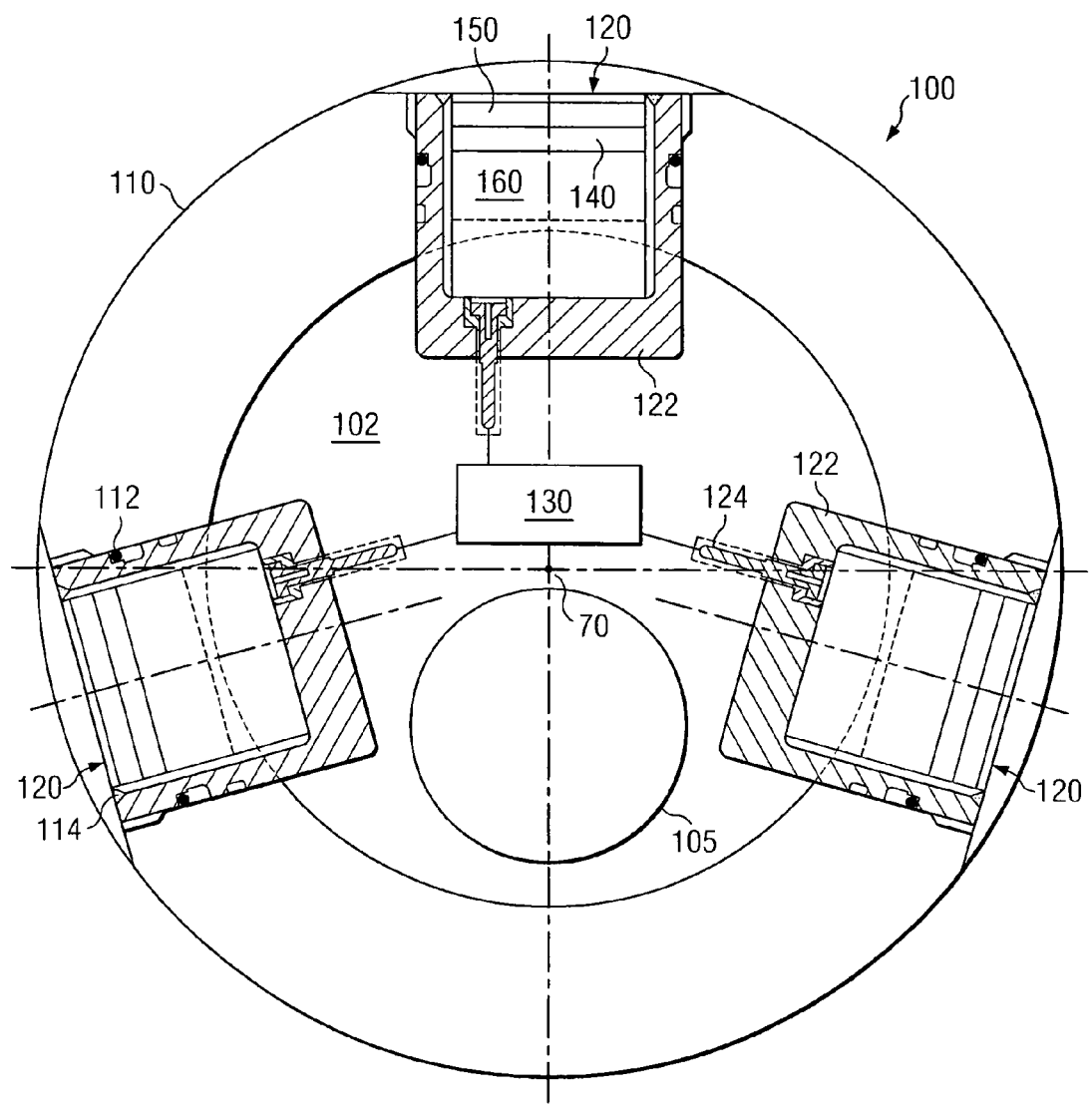
FIG. 3 is a cross sectional view as shown on section 3-3 of FIG. 2.

Referring now to FIG. 3, the exemplary acoustic measurement tool 100 is shown in cross section as illustrated on FIG. 2. As shown on FIG. 3, downhole measurement tool 100 includes three acoustic sensors 120, each of which is disposed in a housing 122. As noted above, however, the invention is not limited to any particular number of acoustic sensors that may be deployed at one time. As described in more detail below, at least one of the acoustic sensors 120 includes a piezo-composite transducer element 140. Acoustic sensors 120 may optionally further include a matching layer assembly 150 for substantially matching the impedance of the piezo-composite transducer 140 with drilling fluid at the exterior of the tool 100 and/or for substantially shielding the piezo-composite transducer element 140 from mechanical damage. The acoustic sensors 120 may optionally further include a backing layer 160 for substantially attenuating acoustic energy reflected back into the tool 100. Exemplary matching layer assemblies and backing layers are described in more detail below with respect to FIGS. 7 through 10.

With continued reference to FIG. 3, the housings 122 are typically fabricated from metallic materials, such as conventional stainless steels, and typically each include one or more sealing members 112, e.g., o-ring seals, for substantially preventing the flow of drilling fluid from the borehole through to the interior 102 of the downhole measurement tool 100. Suitable sealing assemblies include loaded lip seals such as a Polypack® seal, which are available from Gulf Coast Seal & Engineering Corporation (a distributor of Parker Seals), 9119 Monroe Rd, Houston, Tex. 77061. The interface between the housing 122 and the sensors 120 may also include, for example, a molded Viton® bond seal 114 (also available from Gulf Coast Seal & Engineering) for substantially preventing drilling fluid from penetrating into the interior of the housing 122.

With further reference to FIG. 3, the acoustic sensors 120 are coupled via connectors 124, for example, to a controller, which is illustrated schematically at 130. Controller 130 typically includes conventional electrical drive voltage electronics (e.g., a high voltage, high frequency power supply) for applying a waveform (e.g., a square wave voltage pulse) to the piezo-composite transducer 140, which causes the transducer to vibrate and thus launch a pressure pulse into the drilling fluid. Controller 130 typically also includes receiving electronics, such as a variable gain amplifier for amplifying the relatively weak return signal (as compared to the transmitted signal). The receiving electronics may also include various filters (e.g., low and/or high pass filters), rectifiers, multiplexers, and other circuit components for processing the return signal.

With still further reference to FIG. 3, a suitable controller 130 might further include a programmable processor (not shown), such as a microprocessor or a microcontroller, and may also include processor-readable or computer-readable program code embodying logic, including instructions for controlling the function of the acoustic sensors 120. A suitable controller 130 may also optionally include other controllable components, such as sensors, data storage devices, power supplies, timers, and the like. The controller 130 may also be disposed to be in electronic communication with various sensors and/or probes for monitoring physical parameters of the borehole, such as a gamma ray sensor, a depth detection sensor, or an accelerometer, gyro or magnetometer to detect azimuth and inclination. Controller 130 may also optionally communicate with other instruments in the drill string, such as telemetry systems that communicate with the surface. Controller 130 may further optionally include volatile or non-volatile memory or a data storage device. The artisan of ordinary skill will readily recognize that while controller 130 is shown disposed in collar 110, it may alternatively be disposed elsewhere within the measurement tool 100.

As stated above, and with yet further reference to FIG. 3, measurement tool 100 includes at least one acoustic sensor 120 having a piezo-composite transducer element 140. A composite material is generally defined as a synthetically produced material including two or more dissimilar components to achieve a property or properties that are in at least one sense superior to that of any of the constituent components. Known piezo-composite materials are typically fabricated by combining, for example, a piezo-ceramic and a relatively soft (as compared to the piezo-ceramic) non piezoelectric material (e.g., a polymeric material) to achieve a composite material having, for example, superior electromechanical properties. Embodiments of an acoustic sensor of this invention may utilize substantially any piezo-composite transducer element fabricated from substantially any constituents, one of which is a piezoelectric material. For example, the piezo-composite transducer may include a 1-3 piezoelectric-polymer composite including a periodic array of finely spaced piezoelectric posts extending through the thickness of the transducer, with each post surrounded on the sides by a polymer matrix. Alternatively, the piezo-composite transducer may include a 2-2 piezoelectric-polymer composite including alternating two-dimensional strips of piezo-ceramic and polymer disposed side by side or a 0-3 piezoelectric-polymer composite including a piezoelectric powder embedded in a polymer matrix.

Figure 4:
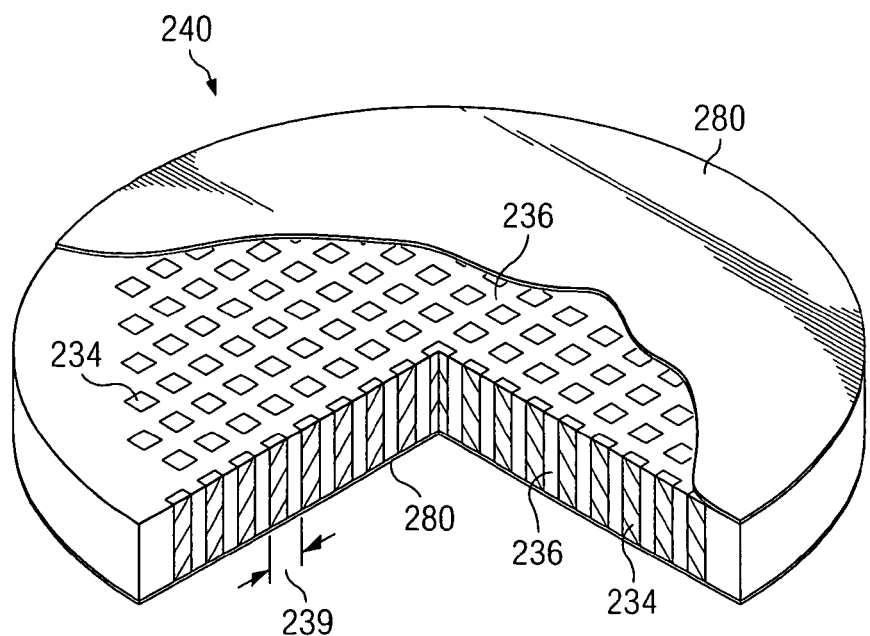
FIG. 4 is a schematic representation, cross sectional perspective view, of one embodiment of a piezo-composite transducer according to the principles of this invention.

Referring now to FIGS. 4 through 9, exemplary acoustic sensors suitable for use in downhole measurement tools (e.g., measurement tool 100 of FIGS. 1 through 3) according to the present invention are illustrated. FIG. 4 shows an exemplary piezo-composite transducer 240 having a composite structure similar to a conventional 1-3 piezo-composite. Piezo-composite transducer 240 is substantially in the form of a disk and includes an array of piezoelectric posts 234 disposed in a non piezoelectric matrix 236. Piezoelectric posts 234 typically extend through the thickness of the transducer 240 in at lest one dimension and may be disposed in substantially any predetermined pattern. While the piezoelectric posts may be disposed in substantially any pattern, a conventional 1-3 pattern including alternating piezoelectric 234 and non piezoelectric 236 posts is often desirable owing to its relative ease of manufacturing (as compared with other, more complex patterns). The piezoelectric posts 234 may have substantially any lateral spacing 239, with finer spacing required for high frequency applications. For most downhole applications a lateral spacing 239 on the order of from about a fraction of to several times the diameter (for cylindrical) or cross-sectional width (for square/rectangular) of the piezoelectric posts is suitable.

Figure 5:
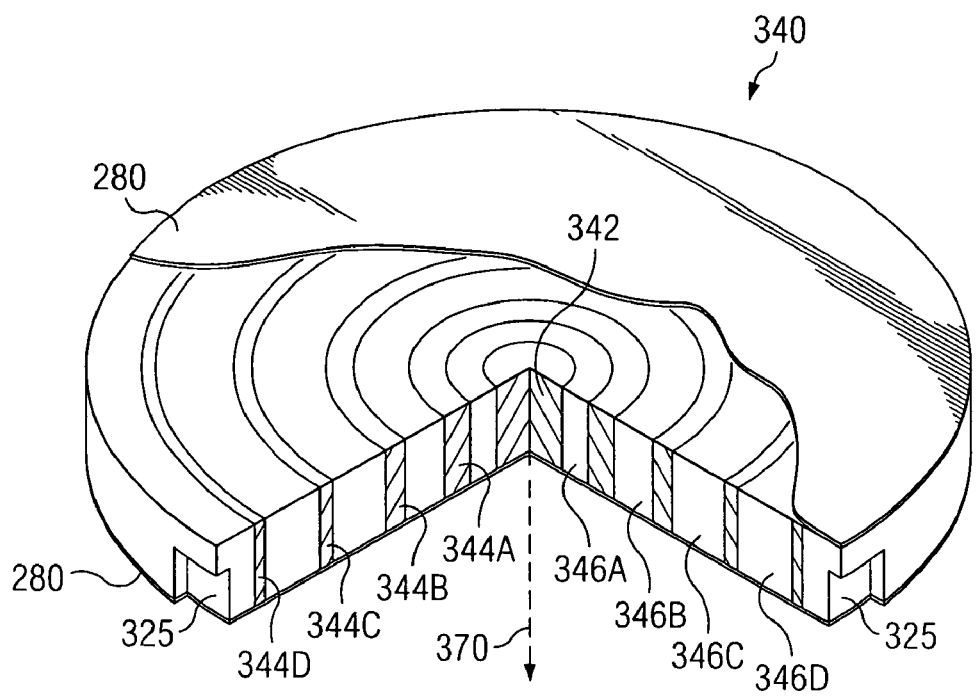
FIG. 5 is a schematic representation, cross sectional perspective view, of another embodiment of a piezo-composite transducer according to the principles of this invention.

Referring now to FIG. 5, an alternative piezo-composite transducer 340 is shown, having a composite structure similar to a conventional 2-2 piezo-composite. Piezo-composite transducer 340 is substantially in the form of a disk optionally including two or more axial slits 325 disposed around the periphery thereof. Transducer 340 preferably includes four axial slits 325 disposed at about ninety-degree intervals. The slits 325 are believed to reduce lateral vibration modes and thus may be desirable for certain piezo-composites (such as 2-2 family composites) and certain downhole applications. While substantially any 2-2 piezo-composite structure may be utilized for exemplary alternating planar layers of piezoelectric and polymer materials, transducer 340 includes a piezoelectric disk 342 about which a plurality of alternating piezoelectric rings 344A, 344B, 344C, and 344D and non piezoelectric rings 346A, 346B, 346C, and 346D are disposed. It will be understood that a general reference herein to the piezoelectric rings 344 and non piezoelectric rings 346 applies collectively to the piezoelectric rings 344A, 344B, 344C, and 344D or non piezoelectric rings 346A, 346B, 346C, and 346D, respectively, unless otherwise stated. Transducer 340 may include substantially any number of concentric piezoelectric rings 344. Typically, the greater the number of concentric rings the better the performance of the piezo-composite (especially at relatively higher frequencies), but with the trade-off of increased fabrication costs. Good performance at a reasonable cost may typically be achieved with two or more piezoelectric rings 344.

In the embodiments shown on FIG. 5, the radial thickness of the piezoelectric rings 344 decreases from the inner ring 344A to the outer ring 344D according to a predetermined mathematical function (e.g., according to a mathematical relation based on standard Gaussian or Bessel functions). Likewise the thickness of the non piezoelectric rings 346 increases from the inner ring 346A to the outer ring 346B. Such varying of the thicknesses of the piezoelectric 344 and/or the non piezoelectric 346 rings is referred to herein as apodization. Such apodization, while not necessary, may be advantageous in that it tends to reduce unwanted sidelobes and non transverse modes of vibration (i.e., vibration modes perpendicular to the cylindrical axis 370 of the transducer 340), thereby increasing the magnitude of the usable acoustic output for a given electrical input.

With continued reference to FIGS. 4 and 5, embodiments of the piezo-composite transducer of this invention may be fabricated from substantially any piezoelectric and non piezoelectric materials that are stable under downhole conditions (e.g., up to about 200 degrees C. and about 25,000 psi). Piezoelectric materials selected from the lead zirconate titanates (PZT) or the lead metaniobates are typically suitable for many downhole applications. For some applications, it may be desirable to utilize piezoelectric materials having a Curie temperature greater than about 250 degrees C. to prevent the piezoelectric material from becoming either partially or fully deployed and thus altering the piezoelectric properties thereof under extreme downhole conditions (e.g., high temperature). Desirable piezoelectric materials also may typically be characterized as having an electromechanical coupling coefficient (k) equal to or greater than about 0.3. Exemplary lead zirconate titanates useful in this invention include PZT5A available from Morgan Electro Ceramics, Inc., 232 Forbes Road, Bedford, Ohio, and K350 available from Keramos Advanced Piezoelectrics, 5460 West 84$^{th}$ Street, Indianapolis, Ind. Exemplary Lead Metaniobates useful in this invention include K81 and K85 available from Keramos Advanced Piezoelectrics and BM940 available from Sensor Technology Limited, P.O. Box 97, Collingwood, Ontario, Canada.

Useful non piezoelectric materials typically include polymeric materials that are resistant to temperatures in excess of 200 degrees C. (i.e., having a glass transition temperature greater than about 200 degrees C.), exhibit low shrinkage on curing, and may be characterized as having a thermal coefficient of expansion (CTE) less than about 100 parts per million (ppm) per degree C. Various useful non piezoelectric materials may also be characterized as having a glass transition temperature above about 250 degrees C. Suitable non piezoelectric materials are further generally resistant to thermal and mechanical shocks and mechanically flexible (i.e., low elastic modulus) and tough (i.e., high fracture toughness) enough to accommodate thermal expansion and stress mismatches between the various layers of the acoustic sensor. Desirable non piezoelectric materials are typically selected from conventional epoxy resin materials such as Insulcast® 125 epoxy resin available from Insulcast®, 565 Eagle Rock Avenue, Roseland, N.J. or Duralco® 4461 epoxy resin available from Cotronics Corporation, 3379 Shore Parkway, Brooklyn, N.Y.

With further reference to FIGS. 4 and 5, piezo-composite transducers useful in embodiments of this invention may be fabricated by substantially any suitable techniques. For example, transducer 240 (FIG. 4) may be fabricated using a process similar to the known dice and fill technique such as disclosed by Smith, Wallace A., SPIE, Vol. 1733, page 10. Using such a process, two sets of substantially orthogonal grooves are cut (e.g., using a diamond saw) in a conventional piezo-ceramic block (e.g., a piezo-ceramic disk). A non piezoelectric (e.g., polymeric) material may then be cast into the grooves. The solid piezo-ceramic base (having a thickness typically ranging from about 0.5 to about 2 millimetres) is then ground (or cut) off and the composite polished to a final thickness (e.g., from about 1 to about 2 millimetres). Electrical communication may be established by substantially any known technique, for example, by sputter depositing a thin layer of gold 280 (shown on FIGS. 4 and 5), for example, on each of the opposing faces of the piezo-composite disk and attaching conventional leads (not shown) thereto.

In an alternative fabrication procedure a piezo-ceramic slurry may be cast (e.g., via conventional injection molding techniques) in a reverse mold. After removal of the piezo-ceramic from the mold, a polymeric material may be cast into the open spaces therein to form the piezo-composite. Any solid piezo-ceramic base may be ground or cut off and the piezo-composite polished to a final thickness as described above. Electrical leads may also be attached as described in the preceding paragraph. Such a fabrication procedure, while typically more expensive than the dice and fill technique described above, may advantageously provide increased flexibility in fabricating more complex piezo-composite structures, such as, for example, piezo-composite transducer 340 shown in FIG. 5.

The artisan of ordinary skill will readily recognize that the above described piezo-composite transducers (shown in FIGS. 4 and 5) are merely exemplary. A wide range of configurations and piezoelectric and non piezoelectric materials may be suitable for downhole applications, depending upon device requirements, cost restraints, the particular downhole conditions, and/or other factors. For example, as described above, acoustic sensors of this invention may utilize substantially any 1-3 or 2-2 type piezo-composites. Additionally, it will be appreciated that embodiments of the piezo-composite transducers of this invention may include other materials (e.g., additional non piezoelectric materials and/or two or more distinct piezoelectric materials).

Figure 6:
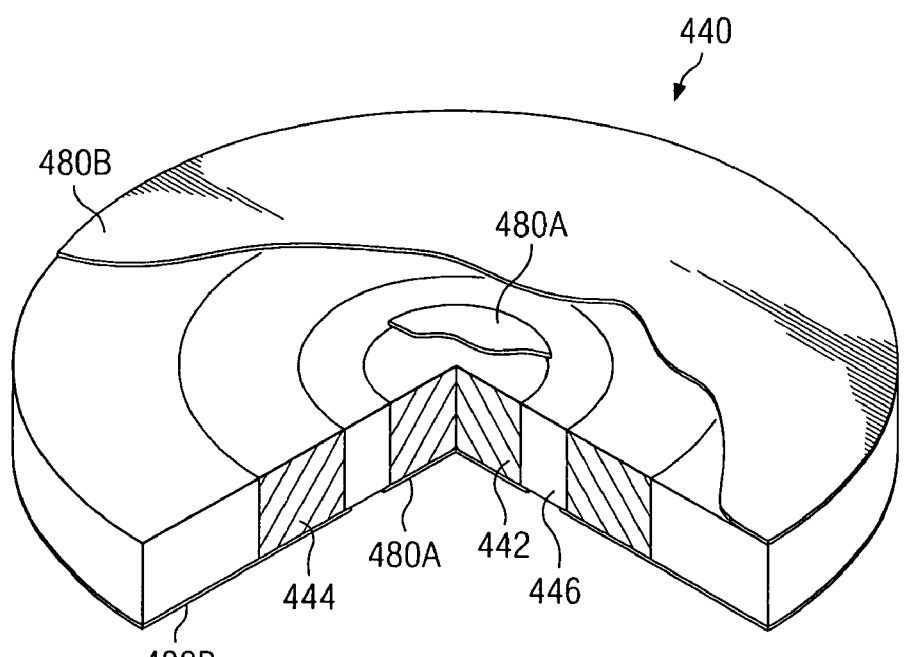
FIG. 6 is a schematic representation, cross sectional perspective view, of still another embodiment of a piezo-composite transducer according to the principles of this invention.

Piezo-composite transducers 240 and 340, as shown in FIGS. 4 and 5, are typically configured for conventional pulse echo ultrasonic measurements. However, piezo-composite transducers, in general, may also advantageously provide for alternative ultrasonic measurement schemes, such as a pitch-catch scheme, in which one portion of the piezo-composite transducer is utilized as a transmitter (i.e., to transmit an ultrasonic signal) and another portion of the transducer is utilized as a receiver (i.e., to receive an ultrasonic signal). Utilization of such a pitch-catch scheme may advantageously reduce, or even eliminate, transducer ringing effects, by substantially electromechanically isolating the transmitter and receiver, and thereby may significantly improve the signal to noise ratio of the transducer. One example of a transducer configured for pitch-catch ultrasonic measurements is shown in FIG. 6. Transducer 440 includes an inner piezoelectric disk 442 and an outer piezoelectric ring 444 separated by a non piezoelectric (e.g., polymer) ring 446. In the embodiment shown, piezoelectric disk 442 may be utilized as a transmitter and electrically coupled to suitable transmitter electronics, for example, via gold layer 480A, while piezoelectric ring 444 may be utilized as a receiver and coupled to suitable receiver electronics, for example, via gold layer 480B. The artisan of ordinary skill will readily recognize that piezoelectric disk 442 may alternatively be utilized as a receiver and piezoelectric ring 444 utilized as a transmitter. As with piezo-composite transducers 240 and 340, (FIGS. 4 and 5) substantially any suitable piezoelectric and non piezoelectric materials may be utilized in fabricating transducer 440. In certain advantageous embodiments, the transmitter may be fabricated from a lead zirconate titanate such as PZT5A available from Morgan Electro Ceramics while the receiver may be fabricated from a lead metaniobate such as K81 or K85, both of which are available from Keramos Advanced Piezoelectrics.

It will be appreciated that substantially any piezo-composite structure may be configured for such pitch-catch ultrasonic measurements, provided that a transmitter portion of the transducer may be substantially electromechanically isolated from a receiver portion thereof. For example, transducer 340, shown in FIG. 5, may be modified such that piezoelectric disk 342 and piezoelectric ring 344A are utilized as a transmitter and piezoelectric rings 344B, 344C, and 344D are utilized as a receiver. This may be accomplished, for example, by attaching separate leads to the transmitter and receiver portions of the piezo-composite, e.g., a first lead coupled to the piezoelectric disk 342 and ring 344A and a second lead coupled to the piezoelectric rings 344B, 344C, and 344D. Likewise, transducer 240, shown in FIG. 4, may be similarly modified such that a portion of the piezoelectric posts 234 are utilized as a transmitter (e.g., the inner posts) and another portion as a receiver (e.g., the outer posts). Of course, in such alternative embodiments of FIGS. 4 and 5, gold layer 280 would have to be modified to provide separate, electromechanically isolated connections to the transmitter and receiver portions.

Figure 7:
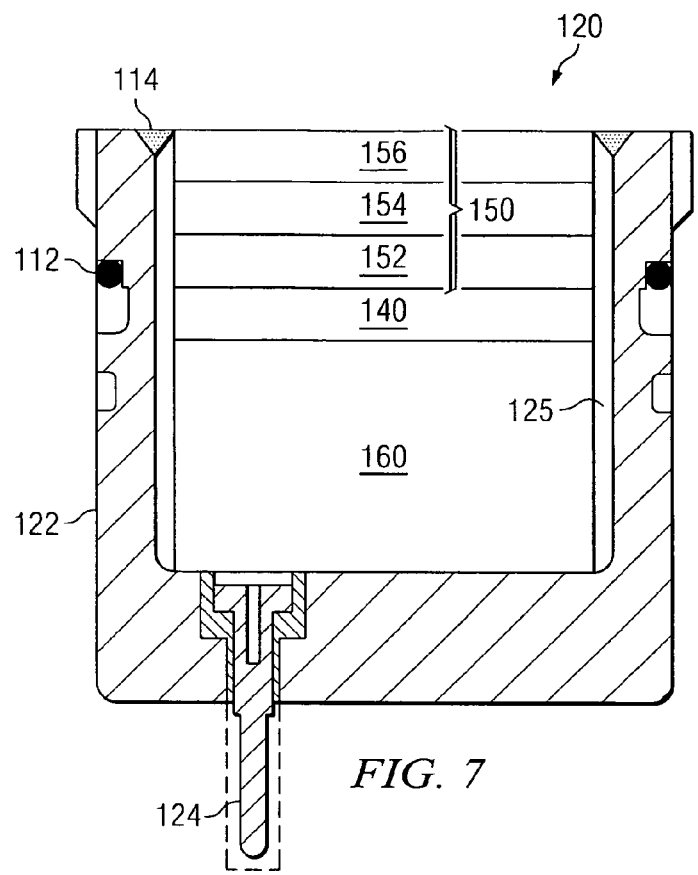
FIG. 7 is a cross sectional schematic representation of the acoustic sensor assembly 120 shown in FIG. 3.

Referring now to FIG. 7, and with further reference to FIG. 3, acoustic sensor 120 is shown in further detail, including corresponding parts 112, 122 and 124 from FIG. 3. Acoustic sensor 120 in this embodiment is a multi-layer device including a piezo-composite transducer 140. As described above, piezo-composite transducer 140 may include substantially any suitable piezo-composite such as one of the exemplary embodiments described above with respect to FIGS. 4 through 6. As shown on FIG. 7, various embodiments of acoustic sensor 120 may optionally include a backing layer 160 for substantially attenuating ultrasonic energy reflected back into the transducer from other components in sensor 120 (rather than outward into the drilling fluid). Various embodiments of acoustic sensor 120 may optionally include a matching layer assembly 150 including at least one each of matching layers 152 and 154 for providing impedance matching between the piezo-composite transducer 140 and the drilling fluid at the exterior of the tool. Embodiments of the matching layer assembly 150 may also include a barrier layer 156 for shielding the piezo-composite transducer 140 from mechanical damage as described in more detail below.

With continued reference to FIG. 7, backing layer 160 typically includes a composite material having a mixture of one or more elastomeric polymer materials (e.g., rubber) and one or more powder materials. Backing layer 160 may include substantially any elastomeric polymer material, advantageously with sufficient high temperature resistance for use in downhole applications. Suitable elastomeric polymer materials also advantageously provide sufficient dampening of back reflected ultrasonic energy at downhole temperatures. Natural rubbers, for example, typically provide sufficient dampening of ultrasonic energy at low temperatures. Various vulcanized rubbers (e.g., sulfur crosslinked elastomers) typically provide sufficient dampening of ultrasonic energy at higher temperatures and thus may be preferable in exemplary embodiments of backing layer 160.

Exemplary backing layers 160 may utilize fluoroelastomer polymers, which generally provide exceptional resistance to high temperature aging and degradation and thus tend to be well suited for meeting the demands of the downhole environment. Fluoroelastomers also tend to dampen ultrasonic energy at temperatures up to and exceeding 250 degrees C. Fluoroelastomers are generally classified into four groups: A, B, F, and specialty. The A, B, and F groups are known to generally have increasing fluid resistance derived from increased fluorine levels (about 66 atomic percent, about 68 atomic percent, and about 70 atomic percent, respectively). Substantially any suitable A, B, F, and/or specialty fluoroelastomer may be utilized in various embodiments of backing layer 160. For example, exemplary backing layers 160 may include group A fluoroelastomers (i.e., those including about 66 atomic percent fluorine), such as Fluorel® brand fluoroelastomers FC 2178, FC 2181, FE 5623Q, or mixtures thereof, available from Dyneon®, Decator, Ala. Other exemplary backing layers may include copolymers of vinylidene fluoride and hexafluoropropylene, such as Viton® B-50, available from DuPont® de Nemours, Wilmington, Del.

Exemplary backing layers may also include substantially any suitable powder material, such as tungsten powers, tantalum powders, and/or various ceramic powders. In one useful embodiment, tungsten powders having a bimodal particle size distribution may be utilized. For example, one exemplary backing layer includes a mixture of C-8 and C-60 tungsten powders available from Alldyne Powder Technologies, 148 Little Cove Road, Gurley, Ala. The particle size of C8 is in the range from about 2 to about 4 microns while the particle size of C60 is in the range from about 10 to about 18 microns.

With further reference to FIG. 7, exemplary backing layers 160 may further include one or more additives that may improve one or more properties of the backing layer 160. For example, acid acceptors are commonly used in fluoroelastomer compounds and are known to enhance the high temperature performance of the fluoroelastomer. Commonly used acid acceptors include magnesium oxide (MgO), calcium hydroxide (CaOH2), litharge (PbO), zinc oxide (ZnO), dyphos (PbHPO3), and calcium oxide (CaO). Calcium oxide is also known to minimize fissuring, improve adhesion, and reduce mold shrinkage of fluoroelastomer compounds. A variety of fillers may also be used, for example, to provide increased viscosity, hardness, and strength. Common fillers for fluoroelastomers include various carbon blacks, such as MT Black N-990, available from Engineered Carbons, Inc., P.O. Box 2831, Borger, Tex. Mineral fillers, such as barium sulfate, calcium silicate, titanium dioxide, calcium carbonate, diatomaceous silica, and iron oxide may also be utilized.

Exemplary backing layers according to this invention have been fabricated according to the following procedure: A bimodal mixture of tungsten powder was prepared by mixing about 1000 grams of C-8 tungsten powder with about 2900 grams of C-60 tungsten powder, both of which are available from Alldyne Powder Technologies. The tungsten powder mixture was cleaned by submerging in a solvent, such as acetone, draining the solvent, and baking at about 160 degrees C. for two or more hours. A fluoroelastomer blend was then prepared by mixing about 300 grams of FC-2181 with about 200 grams of FC-2178, both of which are available from Dyneon®. About 15 grams of magnesium oxide, maglite powder available from Northwest Scientific Supply, Cedar Hill Road, Victoria, BC, Canada, about 70 grams of calcium oxide, R1414, available from Malinckrodt Baker, 222 Red School Lane, Phillipsburg, N.J., about 15 grams of a first carbon black, MT black N-990, and about 15 grams of a second carbon black, N-774, both of which are available from Engineered Carbons, and about 80 grams of a mold release, such as VPA2, available from DuPont® de Nemours, Wilmington, Del., were then added to and blended with the fluoroelastomer blend.

The fluoroelastomer blend, including the above additives, was dissolved in about 1500 grams of a methyl isobutyl ketone (MIBK) solvent. The tungsten powder mixture was then stirred into the solvent mixture. The mixture was stirred frequently (or continuously) to prevent settling of the tungsten powders until about 80 percent or more of the MIBK solvent had evaporated (typically about 1 to 2 hours). Stirring was then discontinued and the mixture allowed to sit for about 12 hours (e.g., overnight) until substantially all of the remaining solvent had been evaporated. The prepared material was then placed in a single cavity mold and hot pressed into the form of a pellet having a thickness of about 2.2 centimeters under a load of about 125,000 kilograms at a temperature of about 165 degrees C.

Backing layers fabricated as described above were found to have excellent stability under typically downhole conditions (e.g., temperatures up to about 200 degrees C. and pressures up to about 25,000 psi). Such backing layers were also found to provide greater than 50 dB attenuation of ultrasonic energy at a frequency band of about 100 kHz.

With further reference to FIG. 7, matching layer assembly 150 typically includes at least one impedance matching layer 152 and a barrier layer 156. In the embodiment of the matching layer assembly shown in acoustic sensor 120, the matching layer assembly includes first and second impedance matching layers 152, 154. First impedance matching layer 152 is typically disposed adjacent the piezo-composite transducer 140 and may be characterized as having an acoustic impedance similar thereto, for example in the range of from about 8 to about 15 MRayl. In one embodiment, first impedance matching layer 152 is fabricated from a glass ceramic, such as a Macor® glass ceramic available from Corning Glass Works Corporation, Houghton Park, N.Y. Glass ceramics may advantageously provide exceptional high temperature resistance as well as a low coefficient of thermal expansion. Glass ceramics also tend to possess favorable mechanical properties and may also function to protect the transducer assembly. In alternative embodiments, first impedance matching layer may be fabricated from a polymeric material (e.g., a conventional epoxy having a suitable acoustic impedance and high temperature resistance). Such an epoxy may also advantageously include fillers, such as various ceramic particles, for reducing the thermal coefficient of expansion and increasing the acoustic impedance of the layer.

With continued reference to FIG. 7, second impedance matching layer 154 is typically disposed adjacent the first impedance matching layer 152 and may be characterized as having an acoustic impedance similar to that of conventional drilling fluid, e.g., on the order of from about 3 to about 7 MRayl. Embodiments of the second impedance matching layer may also be fabricated from conventional epoxy materials, such as Insulcast® 125 available from Insulcast®. Alternative embodiments may be fabricated from composite materials including a mixture of an epoxy and a glass ceramic. For example, in one particular embodiment, a composite including from about 40 to about 80 volume percent Insulcast® 125 and from about 20 to about 60 volume percent Macor® glass ceramic may be utilized. Such a composite may be fabricated, for example, by removing sections of a Macor® glass ceramic disk (e.g., by cutting grooves or drilling holes) and by filling the openings with Insulcast® 125.

With continued reference to FIG. 7, matching layers 152 and 154 may be substantially any thickness depending on the pulse frequency content of the transmitted ultrasonic energy. For typical downhole applications in which the frequency band of the transmitted ultrasonic energy is in the range of from about 100 to about 700 kHz, the thickness of the first impedance matching layer 152 is typically in the range from about 1 to about 2 millimeters, while the thickness of the second impedance matching layer 154 is typically in the range from about 0.8 to about 1.5 millimeters.

Figure 8A:
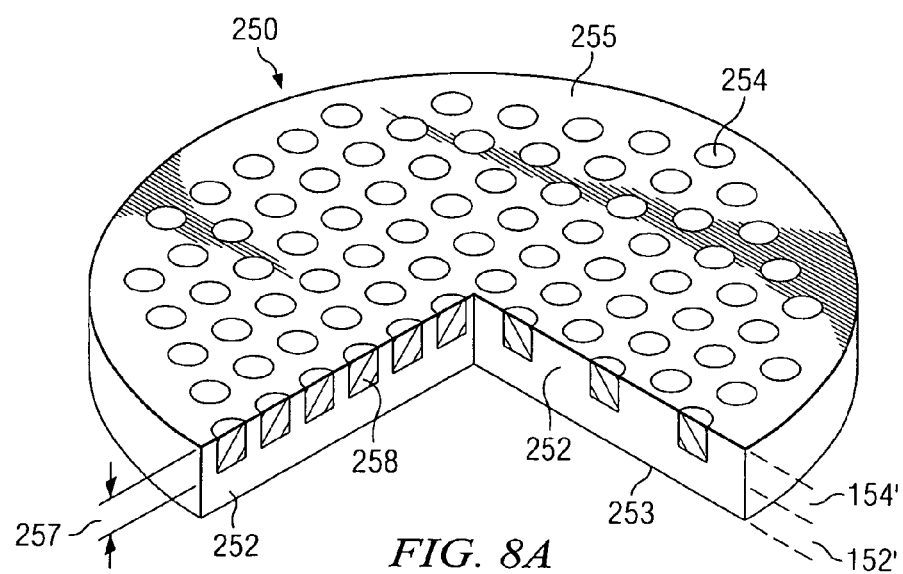
FIG. 8A is a schematic representation, cross sectional perspective view, of one embodiment of the impedance matching layers discussed with respect to FIG. 7.

Referring now to FIG. 8A, it will be appreciated that the first and second impedance matching layers may be fabricated as an integral unit 250. For example, in the embodiments shown, first and second impedance matching layers 152' and 154' may be fabricated from a single a glass ceramic disk 252, e.g., a Macor® disk available from Corning Glass Works. An array of holes 254 (or grooves, cuts, dimples, indentations, etc.) is formed in one face 255 of the disk 252 (for example, by a drilling or cutting operation). The other face 253 of the disk 252 would not undergo such treatment. The holes 254 (or grooves) may penetrate to substantially any depth 257 into the disk, but typically penetrate from about 30 to about 60 percent of the depth thereof. The holes 254 (or grooves, etc.) may further be filled, for example, with a polymer epoxy 258, such as Insulcast® 125, effectively resulting in a two-layer structure, a first impedance matching layer 152' having a relatively higher acoustic impedance (e.g., from about 8 to 15 MRayl) and a second impedance matching layer 154' having a relatively lower acoustic impedance (e.g., from about 3 to about 7 MRayl).

Figure 8B:
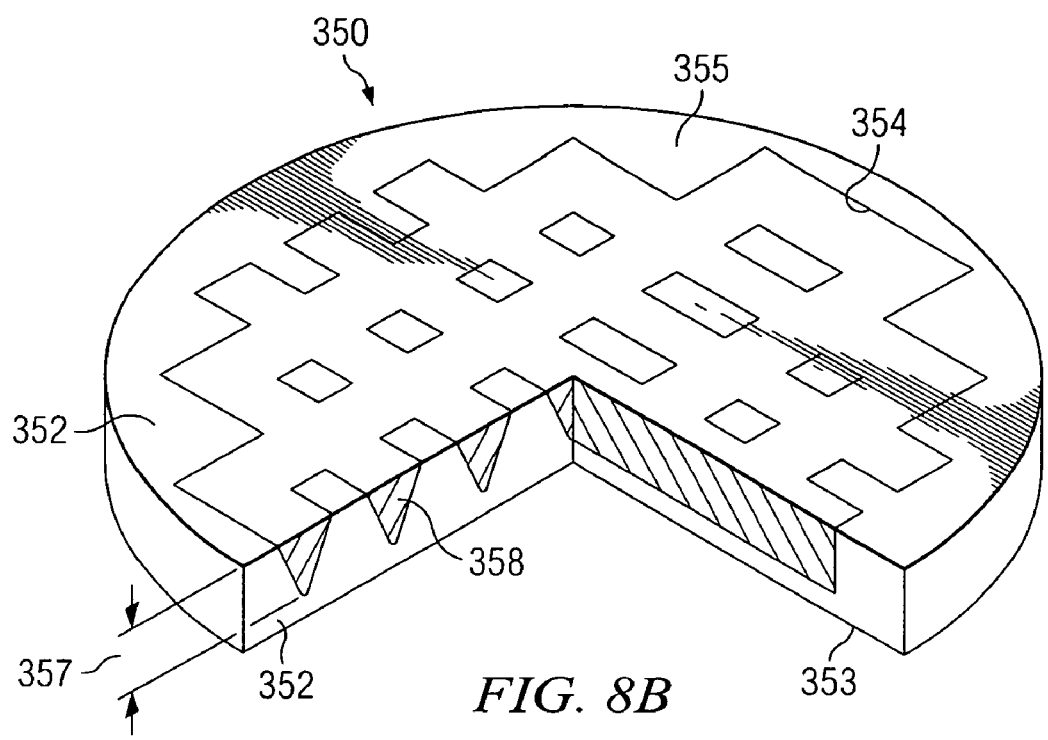
FIG. 8B is schematic representation, cross sectional perspective view, of another embodiment of the impedance matching layers discussed with respect to FIG. 7.

Referring now to FIG. 8B, an alternative embodiment of impedance matching layers is shown. FIG. 8B illustrates a single matching layer 350 having an acoustic impedance that ranges from a relatively higher value (e.g., from about 8 to about 15 MRayl) at a first face 353 to relatively lower value (e.g., from about 3 to about 7 MRayl) at a second face 355. For example, in the embodiments shown, a series of grooves 354 (or holes, cuts, dimples, indentations, etc.) may be formed in one face 355 of a glass ceramic disk 352, such as a Macor® disk. As described above with respect to FIG. 8A, the grooves 354 (or holes, etc.) may be filled with a polymer epoxy 358 such as Insulcast® 125. The grooves 354 are tapered such that the ratio of epoxy (groove or hole area) to ceramic disk increases from the lower face 353 to the upper face 355 thereof. As a result the acoustic impedance also tends to increase from the lower face 353 to the upper face 355, i.e., from about that of the ceramic disk to a fraction thereof depending upon the area fraction of the grooves and the type of polymer epoxy utilized. The grooves 354 may penetrate to substantially any depth 357 into the disk, but typically penetrate from about 60 to about 90 percent of the depth thereof.

During a typical logging while drilling (LWD) measurement cycle, downhole tools (in particular the acoustic sensors 120 disposed in measurement tool 100—FIGS. 1 through 3) may repeatedly impact the sidewall of the borehole or rock cuttings in the drilling fluid. Such impacts to the front face of an acoustic sensor are known in the art to potentially cause various data anomalies. In extreme cases, such impacts are further known to damage the sensors. Provision of a barrier layer having sufficient mechanical strength and wear resistance to minimize such damage may thus advantageously prolong the life of acoustic sensors utilized in downhole environments and/or improve the reliability of acoustic data generated thereby. Provision of such a barrier layer may also enable an outer surface of an acoustic sensor to be flush with an outer surface of the tool body (e.g., tool body 110 in FIG. 3), rather than recessed as in most prior art tools. Sensors provided flush rather than recessed may be advantageous for some downhole applications.

With further reference to FIG. 7, suitable barrier layers 156 may be fabricated from substantially any material having sufficient strength and wear resistance to adequately protect the piezo-composite transducer 140. For example, metallic materials such as titanium and stainless steels may be utilized in embodiments of the barrier layer 156. Alternatively, fiber reinforced composites, such as fiberglass treated with an elastomeric coating, for example, may provide sufficient strength to be utilized in various embodiments of the barrier layer 156. Desirable barrier layers 156 also typically possess sufficiently low acoustic impedance, e.g., less than about 10 MRayl, so as not to overly obstruct transmitted or received ultrasonic energy.

Figure 9A:
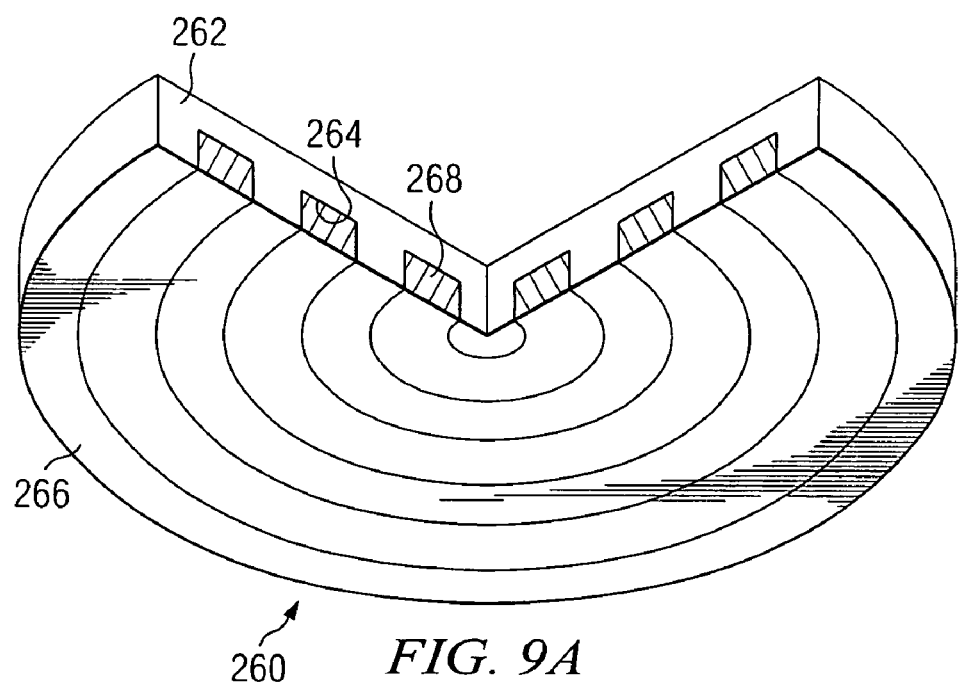
FIG. 9A is a schematic representation, cross sectional perspective view, of one embodiment of the barrier layer discussed with respect to FIG. 7.

Referring now to FIG. 9A, a schematic representation of one embodiment of a barrier layer 260 is illustrated. Barrier layer 260 may be fabricated, for example, from a titanium disk 262, although various other materials such as stainless steels may also be suitable, having a thickness, for example, in a range of from about 0.3 to about 1.2 millimeters. Titanium, while having sufficient mechanical strength, also advantageously includes a relatively low acoustic impedance (as compared, for example, to ferrous materials such as various plain carbon steels and stainless steels). Segmenting the barrier layer, for example as shown, may further reduce the acoustic impedance (e.g., to less than 50 percent of that of a solid disk). In one desirable embodiment, a titanium disk 262 includes a plurality of concentric grooves 264 (or cuts, holes, etc.) formed in one face 266 thereof, with the grooves 264 typically occupying from about 20 to about 40 percent of the cross sectional area of the disk 262. The grooves 294 are typically filled, for example, with a polymeric epoxy resin material 268, such as Insulcast® 125, available from Insulcast® or Viton®, available from E.I. Du Pont de Nemours Company, Wilmington, Del. It will be appreciated that alternative groove patterns may also be utilized, such as, for example, two sets of orthogonal grooves. Embodiments of barrier layer 260 may be, for example, deployed as item 156 and bonded to the second impedance matching layer 154 (FIG. 7) using an adhesive such as Insulbond® 839, available from Insulcast®, with face 262 adjacent matching layer 154.

Figure 9B:
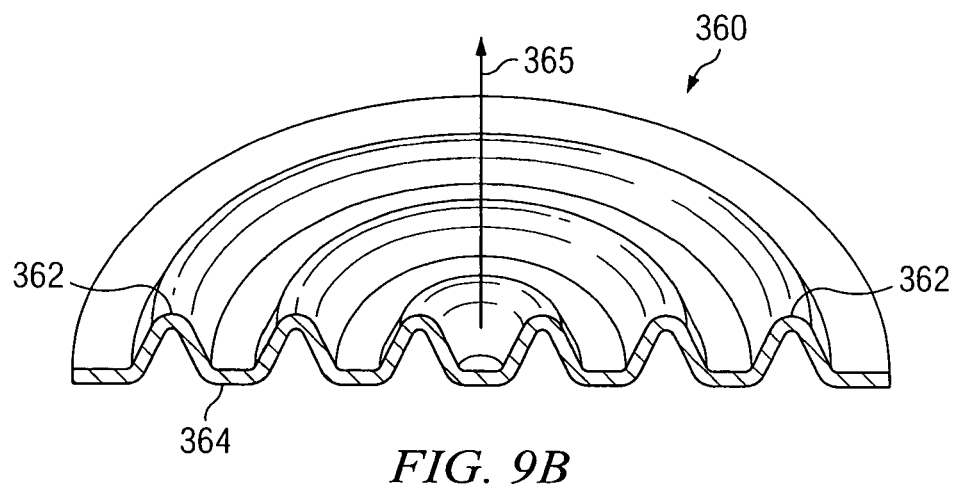
FIG. 9B is a schematic representation, cross sectional perspective view, of another embodiment of the barrier layer discussed with respect to FIG. 7.

Referring now to FIG. 9B, a schematic representation of one alternative embodiment of a barrier layer 360 is illustrated. Barrier layer 360 is similar to barrier layer 260 (FIG. 8A) in that it is fabricated from a titanium disk (or alternatively a stainless steel or other metallic material). Barrier layer 360, differs from that of barrier layer 260, however, in that it is corrugated, for example, by a stamping process. Barrier layer 360 includes a plurality, e.g., from about two to about eight, concentric corrugated grooves 362 disposed therein. The corrugated grooves 362 tend to reduce the strength of the disk along its cylindrical axis 365 and thereby correspondingly tend to reduce the acoustic impedance of the barrier layer 360 (e.g., to less than 50 percent of that of a solid disk). Barrier layer 360 may typically be fabricated by a conventional stamping process (e.g., by stamping face 364) and thus may also advantageously reduce fabrication costs. Barrier layer 360 may also be deployed as item 156 and bonded to the second impedance matching layer 154 (FIG. 7), for example, using an adhesive such as Insulbond® 839, available from Insulcast®, with face 364 adjacent matching layer 154.

Embodiments of the acoustic sensors of this invention may be fabricated by substantially any suitable method. For example, exemplary embodiments of acoustic sensor 120 (FIGS. 3 and 7) have been fabricated according to the following procedure. A backing layer was prepared according to the procedure described above. A 1-3 piezo-composite transducer was prepared according to the dice and fill procedure described above. Teflon® coated leads were then attached to the faces of the transducer (e.g., gold layers 280 in FIG. 4). The piezo-composite transducer was bonded to a front surface of the backing layer using a thin layer (about 0.1 millimeter) of Insulbond® 839 adhesive, available from Insulcast. A matching layer element was fabricated as described above with respect to FIG. 8A. One face (e.g., face 253 in FIG. 8A) of the matching layer element was bonded to the upper surface of the piezo-composite transducer using Insulbond® 839. A corrugated titanium barrier layer was stamped as described above and bonded to the upper surface of the matching layer element using Insulbond® 839. The Teflon® coated leads were then inserted into a slot in the periphery of the backing layer and soldered to corresponding pins mounted on the back side of the backing layer. The sensor assembly was then inserted into a housing. An annular region (e.g., annular region 125 in FIG. 7) around the sensor components and the housing was then filled (e.g., via conventional vacuum filling) with Insulcast® 125 epoxy. A molded Viton® bond seal (e.g., seal 114 in FIG. 7) was then applied around the outer periphery of the annular region.

Figure 10:
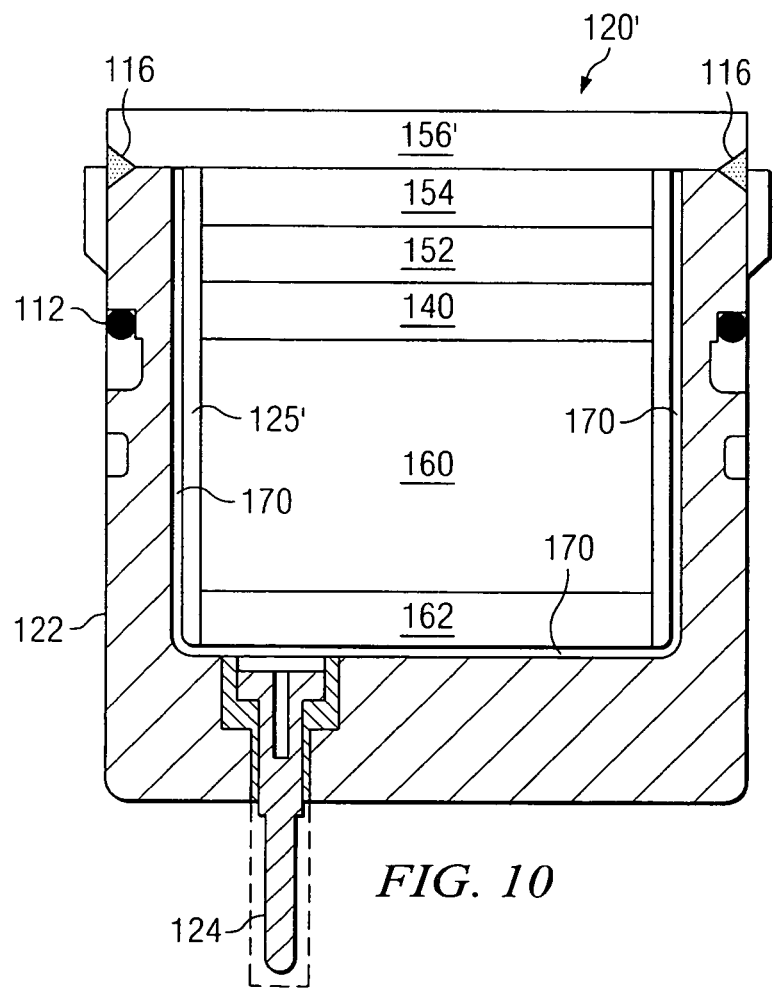
FIG. 10 is a cross sectional schematic representation of an alternative embodiment of an acoustic sensor assembly according to this invention.

Referring now to FIG. 10, a schematic representation of an alternative embodiment of an acoustic sensor 120' is illustrated. Acoustic sensor 120' is substantially similar to that of acoustic sensor 120 (FIGS. 3 and 7) in that it includes a piezo-composite transducer element 140 and other correspondingly-numbered parts. Acoustic sensor 120' differs from acoustic sensor 120 (FIG. 7) in that annular region 125' includes a pressure equalization layer 170 disposed inside the housing 122 and around the sensor components (e.g., components 140, 152, 154, 160, and 162). The pressure equalization layer 170 may include, for example, a thin (e.g. about 0.3 millimeter) layer of silicone oil and may advantageously function to substantially evenly distribute borehole pressure changes about the sensor components. Sensor 120' further differs from sensor 120 (FIG. 7) in that it includes a second backing layer 162 fabricated from a material having a negative thermal expansion coefficient, such as NEX-I or NEX-C glass ceramic available from Ohara Corporation, 23141 Arroyo Vista, Santa Margarita, Calif. Negative thermal coefficient backing layers may advantageously reduce internal stresses resulting from borehole temperature fluctuations and may provide further attenuation of back reflected acoustic energy. Sensor 120' still further differs from sensor 120 (FIG. 7) in that an outer diameter of the barrier layer 156' is chosen to be substantially flush with an outer diameter of the housing. Barrier layer 156' is further typically welded 116 to housing 122 and effectively functions as a faceplate.

While FIGS. 3, 7, and 10 depict acoustic sensors including piezo-composite transducer elements, it will be appreciated that various embodiments of this invention may include a conventional piezo-ceramic transducer element rather than a piezo-composite transducer element. For example, backing layer 160 may advantageously (as compared to prior art backing layers) be utilized in acoustic sensors having conventional piezo-ceramic transducer elements. Likewise, matching layer assembly 150 may advantageously (as compared to prior art matching layers) be utilized in acoustic sensors having conventional piezo-ceramic transducer elements.

Although the present invention and its advantages have been described in detail, it should be understood that various changes, substitutions and alternations can be made herein without departing from the spirit and scope of the invention as defined by the appended claims.

I claim:

1. A downhole measurement tool, comprising:
a substantially cylindrical tool body having a cylindrical axis;
at least one acoustic sensor deployed on the tool body, the acoustic sensor including a piezo-composite transducer element with anterior and posterior faces, the piezo-composite transducer in electrical communication with an electronic control module via conductive electrodes disposed on each of said faces; and
the piezo-composite transducer element including regions of piezoelectric material deployed in a matrix of a substantially non piezoelectric polymeric material, the regions extending through a thickness of the transducer element in at least one dimension, the polymeric material having a glass transition temperature of greater than about 200 degrees C.

2. The downhole tool of claim 1, wherein the piezoelectric material is selected from the group consisting of lead zirconate titanates and lead metaniobates.

3. The downhole tool of claim 1, wherein the piezoelectric material has a Curie temperature greater than about 250 degrees C.

4. The downhole tool of claim 1, wherein the polymeric material comprises an epoxy resin.

5. The downhole tool of claim 1, wherein the regions of piezoelectric material comprise a periodic array of spaced piezoelectric material posts.

6. The downhole tool of claim 5, wherein the piezo-composite transducer element is a product of the process comprising:
providing a piezo-ceramic disk having first and second faces;
cutting a first set and a second set of grooves in the first face, the grooves in the first set being substantially orthogonal to the grooves in the second set, wherein removal of piezo-ceramic material in said groove cutting is operative to shape the piezoelectric material posts;
casting the non piezoelectric material into the grooves to form, in combination with the piezo-ceramic disc, a specimen of piezo-composite material having first and second faces corresponding substantially to those of the piezo-ceramic disk;
polishing the specimen to a predetermined thickness; and
disposing conductive electrodes on each of the first and second faces of the specimen.

7. The downhole tool of claim 1, wherein the piezo-composite transducer element includes alternating concentric rings of the piezoelectric material and the non piezoelectric material disposed about a central element of the piezoelectric material.

8. The downhole tool of claim 7, wherein each of the rings of the piezoelectric material has a predetermined radial thickness selected to decrease with increasing distance from the central element.

9. The downhole tool of claim 8, wherein the radial thickness of the rings of piezoelectric material is selected to decrease according a mathematical function selected from the group consisting of Bessel functions and Gaussian functions.

10. The downhole tool of claim 7, wherein the piezo-composite transducer element comprises a plurality of axial slots formed in a periphery of the transducer.

11. The downhole tool of claim 7, wherein the piezo-composite transducer element is a product of the process comprising:
providing a piezo-ceramic slurry;
casting the piezo-ceramic slurry in a reverse mold to form the concentric rings of piezoelectric material about the central element;
casting the non piezoelectric material in open spaces between the concentric rings of piezoelectric material to form, in combination with the concentric rings of piezoelectric material, a specimen of piezo-composite material having first and second faces;
polishing the specimen to a predetermined thickness; and
disposing conductive electrodes on each of the first and second faces of the specimen.

12. The downhole tool of claim 1, wherein:
the piezo-composite transducer element includes first and second separate piezoelectric elements, the first piezoelectric element serving as a transmitter, the second piezoelectric element serving as a receiver; and
the first and second piezoelectric elements are substantially isolated electromechanically from one another by a non piezoelectric material.

13. The downhole tool of claim 12, wherein the first piezoelectric element includes a lead zirconate titanate piezoelectric material and the second piezoelectric element includes a lead metaniobate piezoelectric material.

14. The downhole tool of claim 1, wherein the conductive electrodes comprise gold.

15. The downhole tool of claim 1, in which the downhole tool is selected from the group consisting of logging while drilling tools and measurement while drilling tools.

16. An acoustic sensor, comprising:
a piezo-composite transducer element including regions of piezoelectric material deployed in a matrix of a substantially non piezoelectric polymeric material, the regions extending through a thickness of the transducer element in at least one dimension;
the polymeric material having a glass transition temperature of greater than about 200 degrees C.;
the piezoelectric material having a Curie temperature greater than about 250 degrees C.; and
the acoustic sensor being configured for use in a downhole measurement tool.

17. The downhole tool of claim 16, wherein the regions of piezoelectric material comprise a periodic array of spaced piezoelectric material posts.

18. The downhole tool of claim 16, wherein the piezo-composite transducer element includes alternating concentric rings of the piezoelectric material and the non piezoelectric material disposed about a central element of the piezoelectric material.

19. The downhole tool of claim 16, wherein:
the piezo-composite transducer element includes first and second separate piezoelectric elements, the first piezoelectric element serving as a transmitter, the second piezoelectric element serving as a receiver; and
the first and second piezoelectric elements are substantially isolated electromechanically from one another by a non piezoelectric material.

20. A method for fabricating a downhole measurement tool, the method comprising:
(a) providing a substantially cylindrical tool body having an electronic control module, the tool body being couplable with a drill string;
(b) providing at least one acoustic sensor including a piezo-composite transducer element with anterior and posterior faces, the piezo-composite transducer element including regions of piezoelectric material deployed in a matrix of substantially non piezoelectric polymeric material, the regions extending through a thickness of the transducer element in at least one dimension; the polymeric material having a glass transition temperature of greater than about 200 degrees C., the piezo-composite transducer element further including conductive electrodes disposed on each of said faces;

(c) deploying the at least one acoustic sensor on the tool body in electrical communication with the electronic control module via said conductive electrodes, the at least one acoustic sensor operable to transmit and receive acoustic signals in a borehole.

* * * * *